US011458335B1

United States Patent
Gordeeva et al.

(10) Patent No.: US 11,458,335 B1
(45) Date of Patent: Oct. 4, 2022

(54) RADIATION DELIVERY SYSTEM IN A MEDICAL APPARATUS FOR ORTHOVOLTAGE RADIATION THERAPY

(71) Applicant: ADANI Systems, Inc., Alexandria, VA (US)

(72) Inventors: Natalia Nikolaevna Gordeeva, Minsk (BY); Vladimir Nikolaevich Linev, Minsk (BY); Alexandr Ivanovich Sheleg, Minsk (BY); Aliaksandr Feliksovich Drazdou, Minsk (BY); Dzmitry Vladimirovich Zaikin, Minsk (BY)

(73) Assignee: LINEV SYSTEMS US, INC., Alexandria, VA (US)

( * ) Notice: Subject to any disclaimer, the term of this patent is extended or adjusted under 35 U.S.C. 154(b) by 0 days.

(21) Appl. No.: 17/406,740

(22) Filed: Aug. 19, 2021

(30) Foreign Application Priority Data

Apr. 30, 2021 (EA) .................................. 202191260

(51) Int. Cl.
 *A61N 5/10* (2006.01)
(52) U.S. Cl.
 CPC ......... *A61N 5/1064* (2013.01); *A61N 5/1045* (2013.01); *A61N 5/1075* (2013.01); *A61N 2005/1095* (2013.01)
(58) Field of Classification Search
 None
 See application file for complete search history.

(56) References Cited

U.S. PATENT DOCUMENTS

| 8,077,830 | B2* | 12/2011 | Brown | A61N 5/1048 |
| | | | | 378/205 |
| 2007/0076851 | A1* | 4/2007 | Pellegrino | G21K 1/10 |
| | | | | 378/65 |
| 2014/0048727 | A1* | 2/2014 | Huntzinger | G21K 1/10 |
| | | | | 250/503.1 |

* cited by examiner

*Primary Examiner* — Hoon K Song
(74) *Attorney, Agent, or Firm* — Bardmesser Law Group

(57) ABSTRACT

Radiation therapy delivery system, including X-ray source, magnetic body rotation fixation node and/or mechanical body rotation fixation node; filter unit with a plurality of filters and a plug that circle a cylindrical element; drive unit for rotating filter unit; collimation elements in a collimation unit body, that includes collimation element fixation device and collimation photoelectric identification system; and processor controlling the filter unit to adjust X-ray filtration characteristics. The filter unit includes filter photoelectric identification system, controller, and photoelectric sensors. The cylindrical element includes slits located on rings that run along outer surface. Photoelectric sensors are triggered by a light beam that passes through the slits to identify/ position filters. First ring with first photoelectric sensor identifies zero position of the filter, second ring with second photoelectric sensor identifies filter working positions, and third ring with a set of slits for each filter, and third photoelectric sensor for filter identification.

7 Claims, 11 Drawing Sheets

RADIATION DELIVERY SYSTEM IN A MEDICAL APPARATUS FOR ORTHOVOLTAGE RADIATION THERAPY

CROSS REFERENCE TO RELATED APPLICATIONS

This application claims priority to Eurasian Patent Application No. 202191260, filed on Apr. 30, 2021, which is incorporated herein by reference in its entirety.

FIELD OF THE INVENTION

The present invention relates to medical equipment, particularly to X-ray machines, and is primarily designed for short-focus radiation therapy used to treat patients with dermatologic, urologic, rheumatic, and oncological ailments.

DESCRIPTION OF THE RELATED ART

Medical equipment comprises a wide selection of diagnostic and therapeutic apparatuses that utilize various sources of ionizing radiation, such as X-ray tubes, natural or artificial isotopes, or particle accelerators. For instance, one conventional apparatus is the Xstrahl 150 stationary X-ray therapy machine [1]. This apparatus comprises a 150 kV metal-ceramic X-ray tube with medical collimation elements. The generator comprises a metal-ceramic X-ray tube with a grounded cathode, a built-in high-voltage connector, and a water cooling system. Xstrahl 150 is a high-energy apparatus for short-focus therapy. The apparatus is designed for stationary use in a radiotherapy department and can be suspended from the ceiling or mounted on a floor stand. The apparatus is controlled via a controllable PC interface with an X-ray control panel and a TP2 control panel. The system operates in the radiation time control mode and is equipped with two CPU-based elements as a backup to an independent countdown timer to ensure safety. The TP2 control panel comprises a two-channel control system in accordance with IEC60601-2-8.

In the time control mode, these are timers that operate in parallel with each other. The system continuously monitors actual voltage (in kV) and current (in mA). If these values deviate by more than ±3%, then the apparatus shuts off automatically. The apparatus is used to treat basal cell epitheliomas, squamous cell carcinoma, keloid scars.

A drawback of Xstrahl 150 is that it lacks automation in its filter and collimation element identification systems, which makes the use of the apparatus more complicated and somewhat inconvenient for users.

Another conventional apparatus is an X-ray therapy machine with an X-ray tube and a generator [2]. The apparatus is designed so that filters can be replaced, and has a collimation tube comprising a neck and a flange connector. The neck of the collimation tube is made of leaded glass, and the perimeter of its end surface is covered with an elastic layer. The apparatus is mounted on a floor stand and connected to a high-voltage generator and a cooling system, both of which are connected to the control panel. There is a through hole in the wall of the neck, a pipe and a flexible tube that connect the hole to a negative-pressure source, which is connected to the control panel and is wired to the air pressure sensor located on the inner surface of the collimation tube neck. This apparatus provides effective radiation therapy for skin diseases that are complicated with suppuration, as vacuum pumping facilitates the drainage of pus from the wound.

The drawback of this conventional apparatus is that it lacks a filter identification system, which makes the use of the apparatus more complicated when treating a patient.

Reference [3] discloses a system for surface radiation therapy with a reduced risk of delivering large doses of radiation on the skin or just under it. The system comprises a generator unit that responds to a control signal indicating the intended radiation level, a collimation element unit that is mechanically coupled with the generator unit, used to receive radiation and apply it as the actual radiation level at a predetermined location—the target area of the patient's body, as well as to reduce the risk that the actual radiation level is different from the intended radiation level. The risk mitigation unit comprises a radiation control detector, a node for orienting the radiation control detector against the generator unit, a test radiation detector, which produces a detector signal that corresponds to the actual radiation level, and a control signal controller, which produces a control signal indicating the intended radiation level or responds to the detector signal that corresponds to the actual radiation level. The radiation control detector is coupled with the generator unit via the same mechanical coupling that is used to connect the generator unit with the collimation element used to deliver radiation to the patient. The radiation control detector comprises a magnet installed at the proximal end, and the radiation therapy system further comprises a sensor that emits signals in case a magnet has been detected, thereby indicating whether the radiation control detector is connected to the generator unit. The risk mitigation unit comprises one or more magnets in an attachment, wherein each magnet is located in a location that corresponds to a possible position of one or more sensors. If a magnet is detected, it thereby indicates whether the radiation control detector is connected to the generator unit.

The drawback of this conventional device is that magnetic field does not provide the required sensor location control precision, which makes magnetic collimation element identification not efficient enough.

Reference [4] describes radiation therapy system with a rotating filter. The system comprises a source of radiation with a filtering device that has a plurality of filters with different filtration characteristics. The focal point of the source of radiation is located inside the filtering device, and the filtering device is adapted to rotate around the focal point in order to change filtration characteristics in response to the control signal. The filter unit has a cylindrical element with a plurality of filters in a circular arrangement inside the cylinder, and a drive unit to rotate the filter unit around the focal point in response to the control signal to change its filtration characteristics. The filter unit comprises at least one filter, a radiation blocker, or a combination thereof. The drive unit comprises a motor and a gear train that is connected to a corresponding gear train in the filter unit for its rotation. The system further comprises a processing module that responds to the user input and produces a control signal to change the filtration characteristics, including output radiation indication before treating the patient, as well as a user input console. The user input comprises data that are used to determine filter settings. The filter unit comprises at least one filtering medium which can change its filtration characteristics in response to the control signal. The filtration characteristic changes include changing the density of the filtering medium. The system further comprises a collimation element unit that is mechanically coupled with the generator unit, used to receive radiation and apply it as the actual radiation level at a predetermined location—the target area of the patient's body.

The drawback of this device is the low accuracy of the filter and collimation element identification system, which makes the use of the apparatus more complicated when treating a patient and increases the risks associated with precise localization of radiation on the target area of the patient's body.

SUMMARY OF THE INVENTION

An object of the present invention is to eliminate these drawbacks and make radiation delivery to a given target area of the patient's body safer.

Another object of the present invention is to increase the accuracy of identifying filters and collimation elements, as well as to make radiation delivery to the target area of the patient's body safer.

To achieve these objectives, there is provided a radiation delivery system in a medical apparatus for radiation therapy that comprises a generator module with an X-ray tube as a source of radiation, a filter unit with a plurality of filters and a plug that circle a cylindrical element, a drive unit for the filter unit, collimation elements, a data input console, and a data processing and output module that outputs control signals to adjust X-ray filtering characteristics. As described herein, the filter unit is equipped with a filter photoelectric identification system and a controller, and comprises photoelectric sensors, wherein the cylindrical element of the filter unit is equipped with slotted rings that run along its outer surface, and photoelectric sensors are located so as to be triggered by a light beam that passes through the slits in order to identify or position the filters, wherein one of the slotted rings with a separate photoelectric sensor is set aside for the zero position of the filter in the filter unit, another groove with a separate photoelectric sensor is set aside for the working positions of the filters, and yet another groove with a unique set of slits for each filter, equipped with photoelectric sensors, is set aside for filter type identification; wherein collimation elements are installed in a collimation unit body, which is equipped with a collimation element fixation device, a collimation element photoelectric identification system, and/or an LED lighting device; and wherein the generator module with the X-ray tube installed in its body and is equipped with a magnetic body rotation fixation node and/or a mechanical body rotation fixation node.

The filters have spherical shapes, their segmented surface area is $S_s = 2\pi RH$ from X to Y cm$^2$ (see FIG. 1 and FIG. 7) and are adapted to homogeneous filtering of X-ray radiation.

The cylindrical element is drum-shaped; it is equipped with two rolling bearings and connected to a gear motor of the drive unit capable of rotating the filter unit via a gear train.

The magnetic rotation fixation node of the body with the X-ray tube comprises electromagnets or an electromagnetic clutch, and the mechanical fixation node comprises a clamping handle, a right drive axle with a handle rotation limiter, as well as a left drive axle, a right clamp and a left clamp that come into contact with the braking surface of the body with the X-ray tube.

The collimation unit is equipped with a collimator used to generate parallel X-ray beams and comprises a lock fixed on an axis, and the collimation element fixation device comprises a conical guide and an eccentric mechanism with an eccentric located on the rotation handle axis.

The collimation element photoelectric identification system is designed to identify the collimation elements, and for that purpose, each collimation element has a unique set of cylindrical rings, which are functionally coupled with the filter identification system via the controller.

The collimation element identification system is functionally coupled with the module for processing and outputting data from the data input console and is adapted to provide the X-ray beam with a given energy.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention and, together with the description, serve to explain the principles of the invention.

DETAILED DESCRIPTION OF THE PREFERRED EMBODIMENTS

Reference will now be made in detail to the preferred embodiments of the present invention, examples of which are illustrated in the accompanying drawings.

Figure 1:
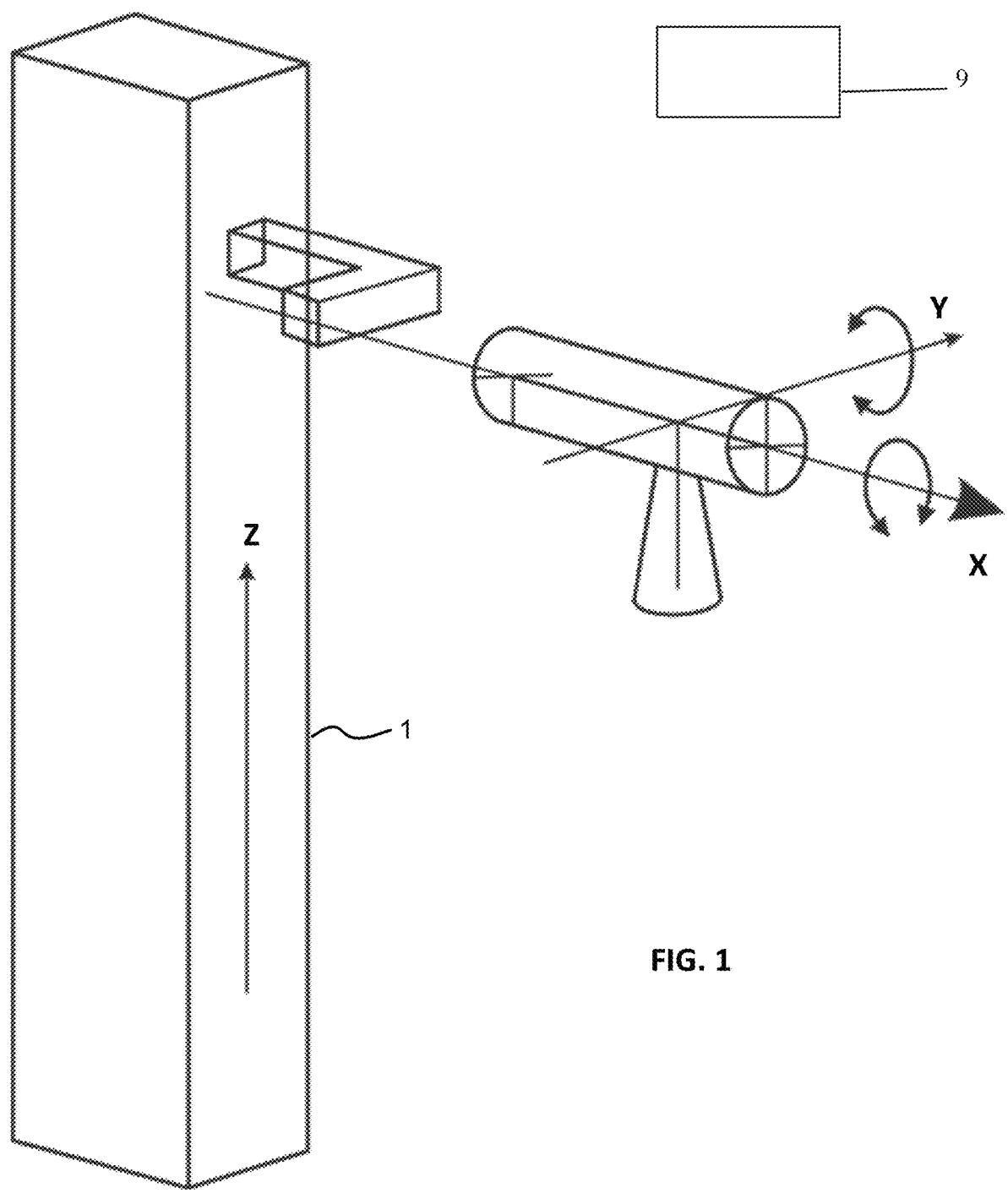
FIG. 1 shows a general view of the radiation delivery system in a medical apparatus.
Figure 2:
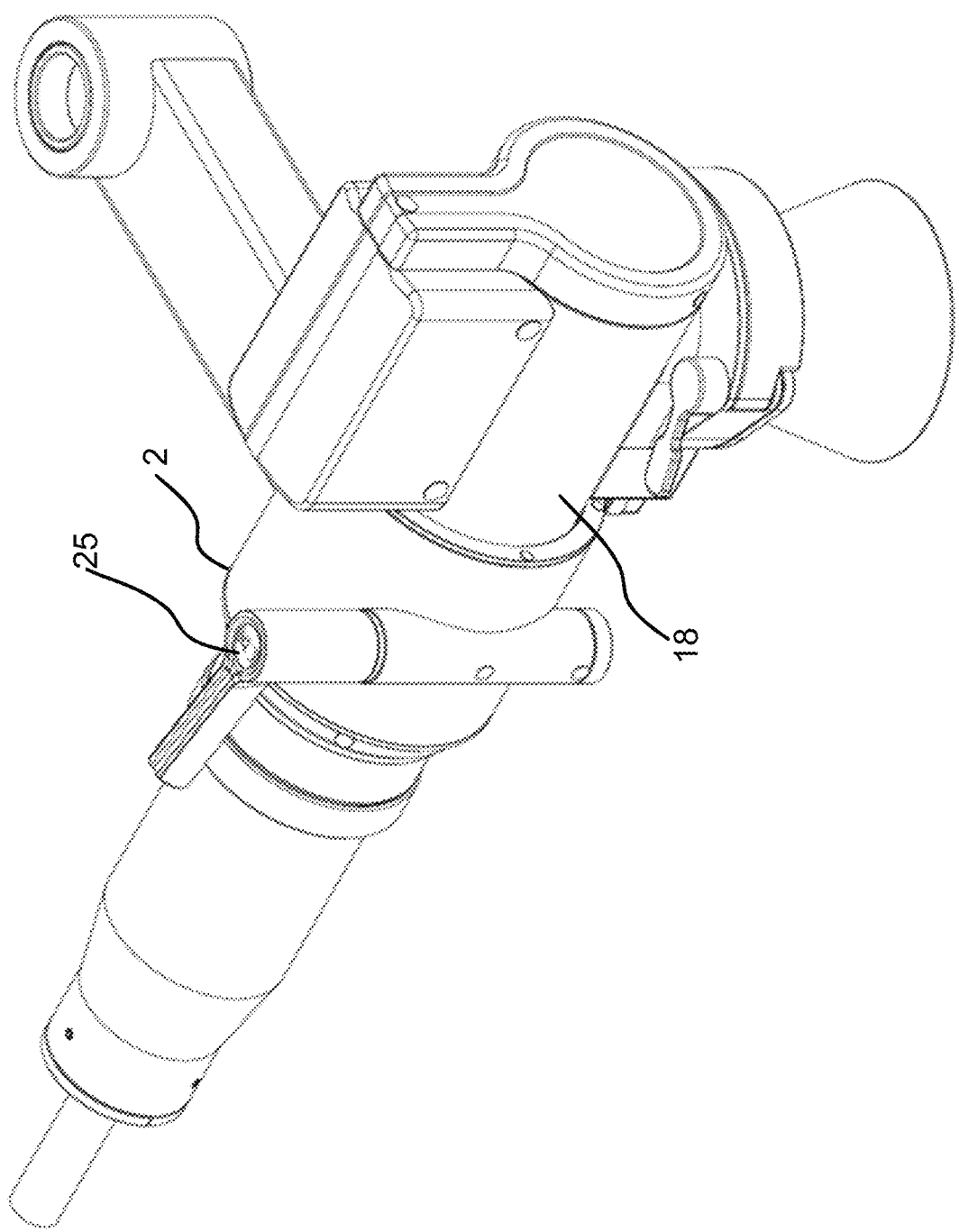
FIG. 2 shows a general view of the generator module.
Figure 3:
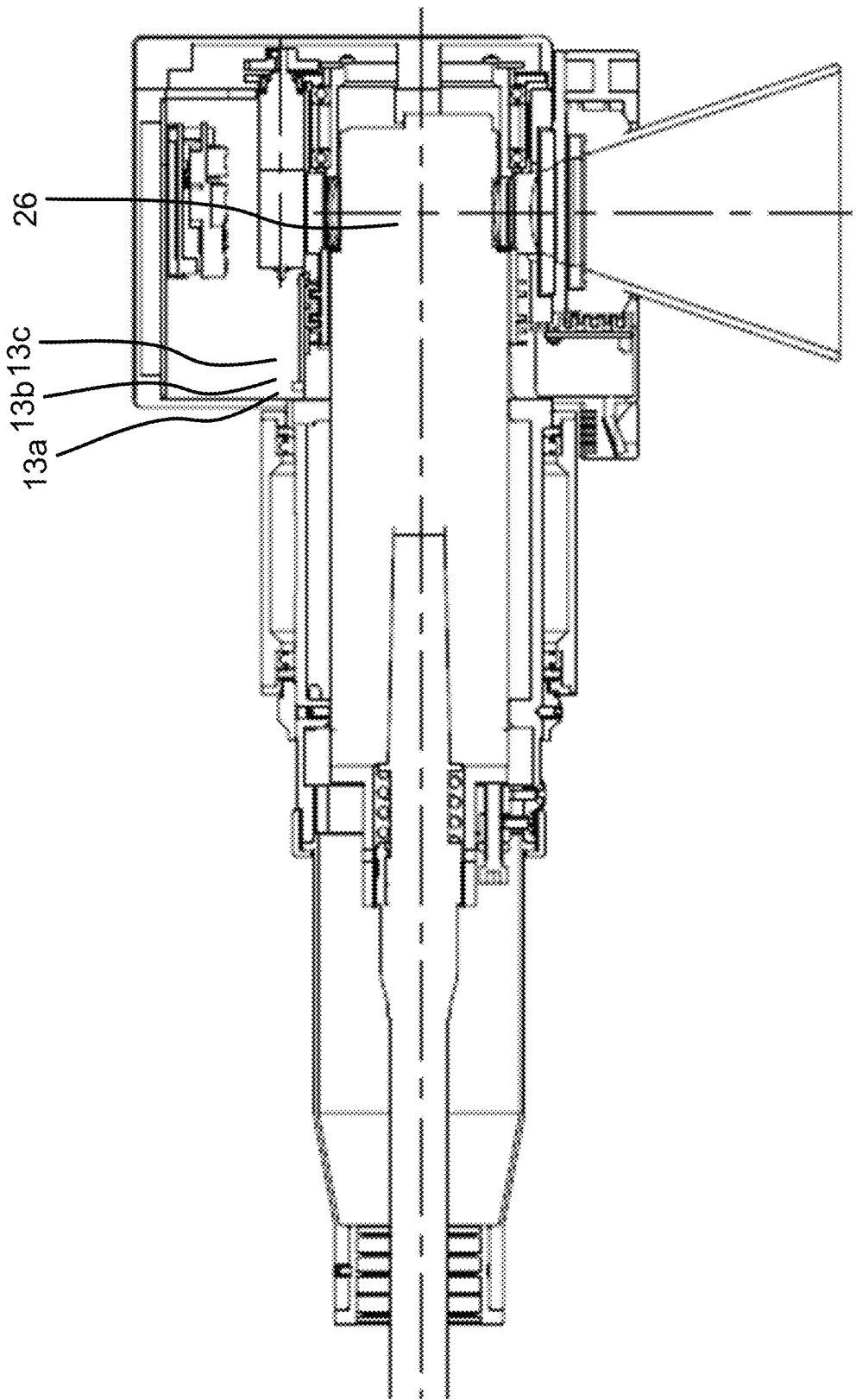
FIG. 3 shows a longitudinal section of the generator module shown in FIG. 2.
Figure 4:
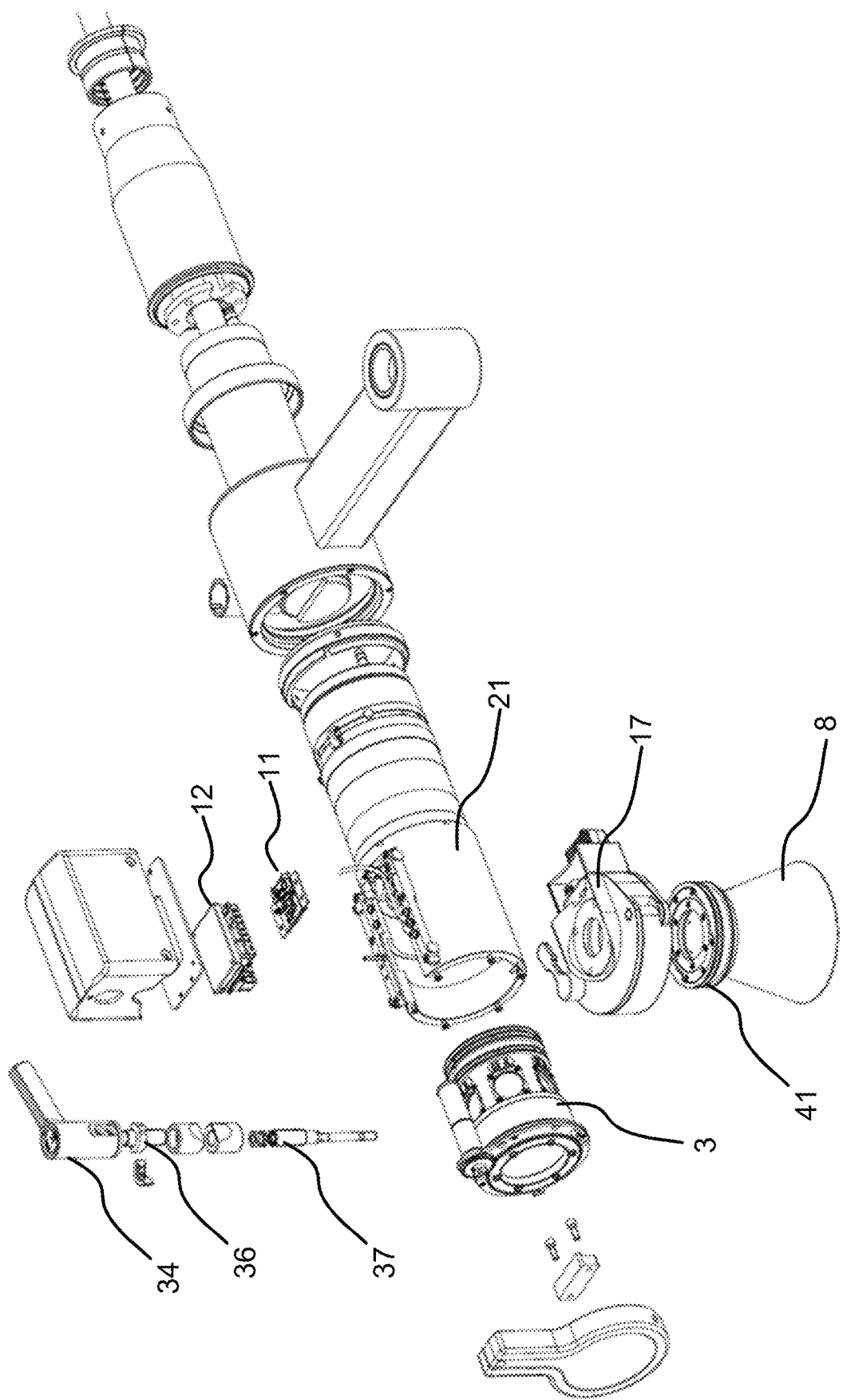
FIG. 4 shows the assembly of the generator module shown in FIG. 2.
Figure 5:
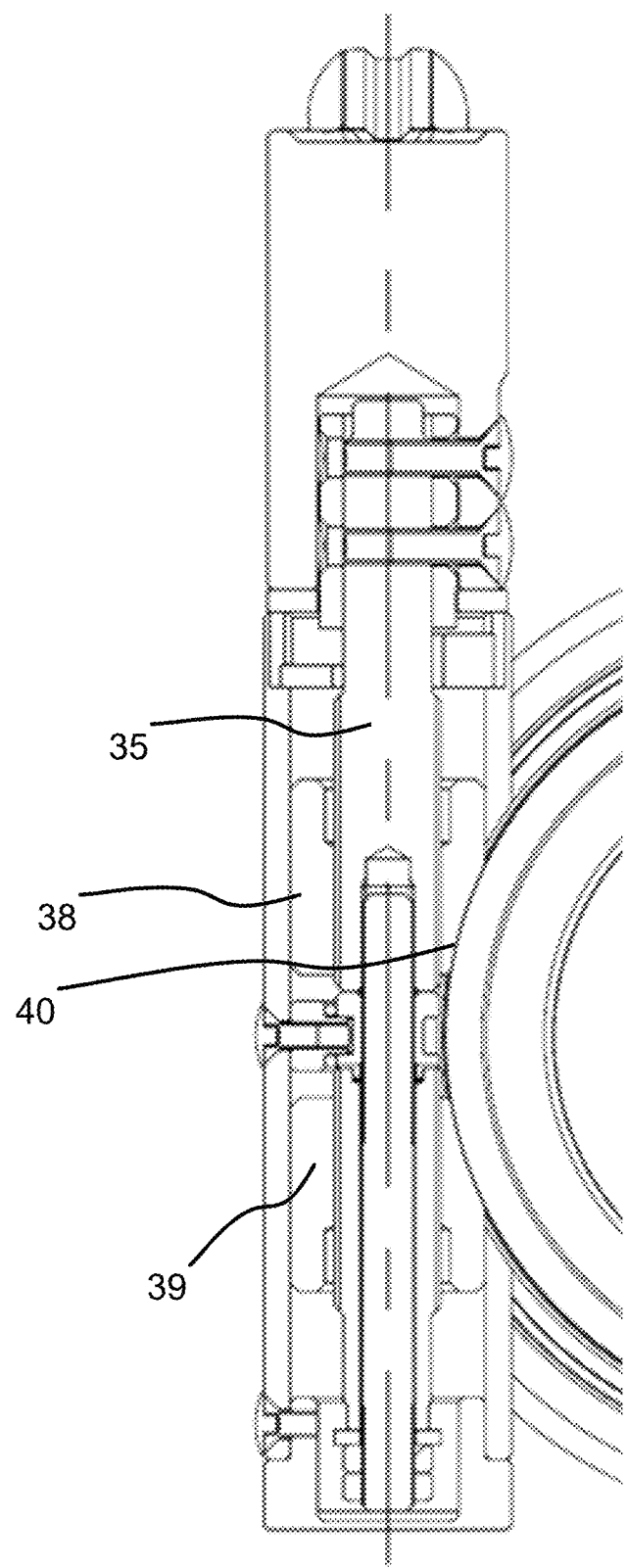
FIG. 5 shows a cross-section fragment of the X-ray tube rotation fixation node.
Figure 6:
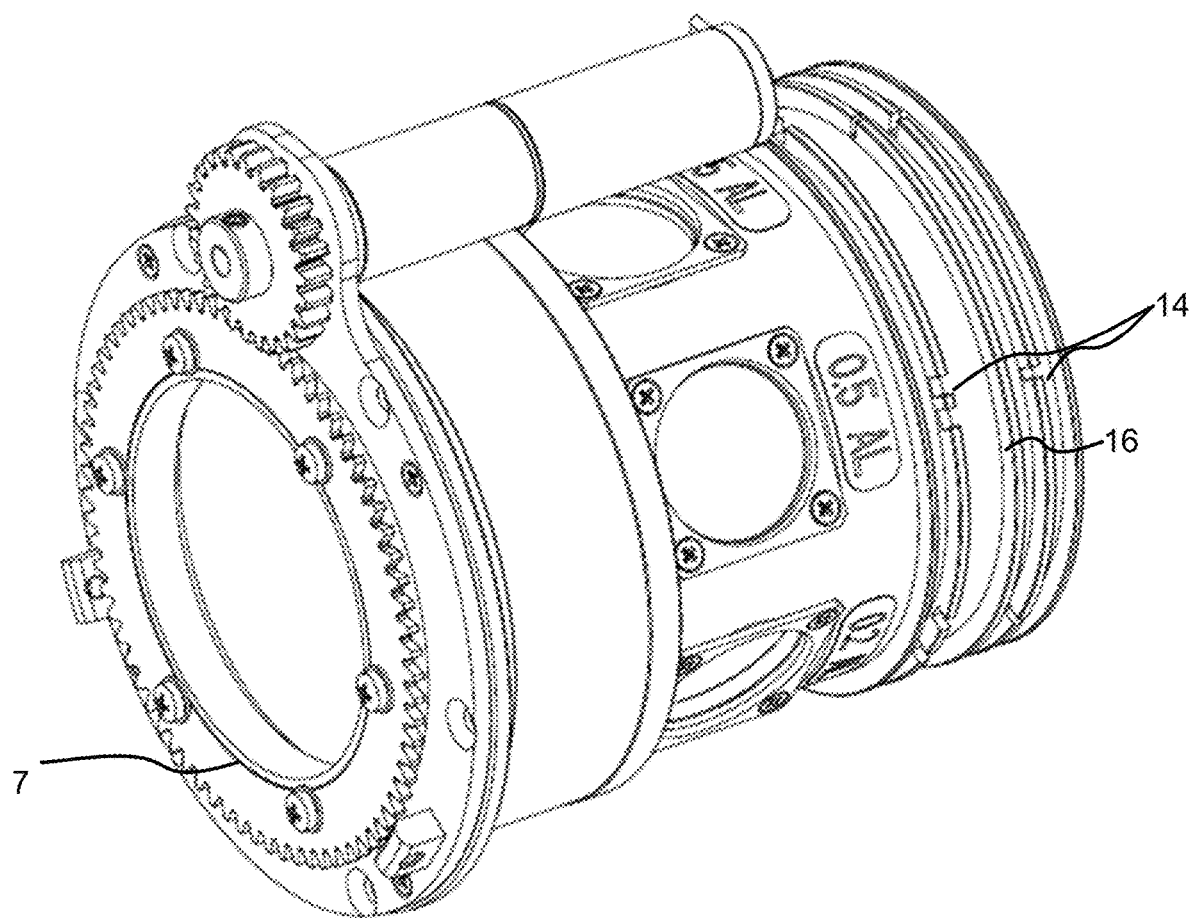
FIG. 6 shows a general view of the cylindrical element of the filter unit.
Figure 7:
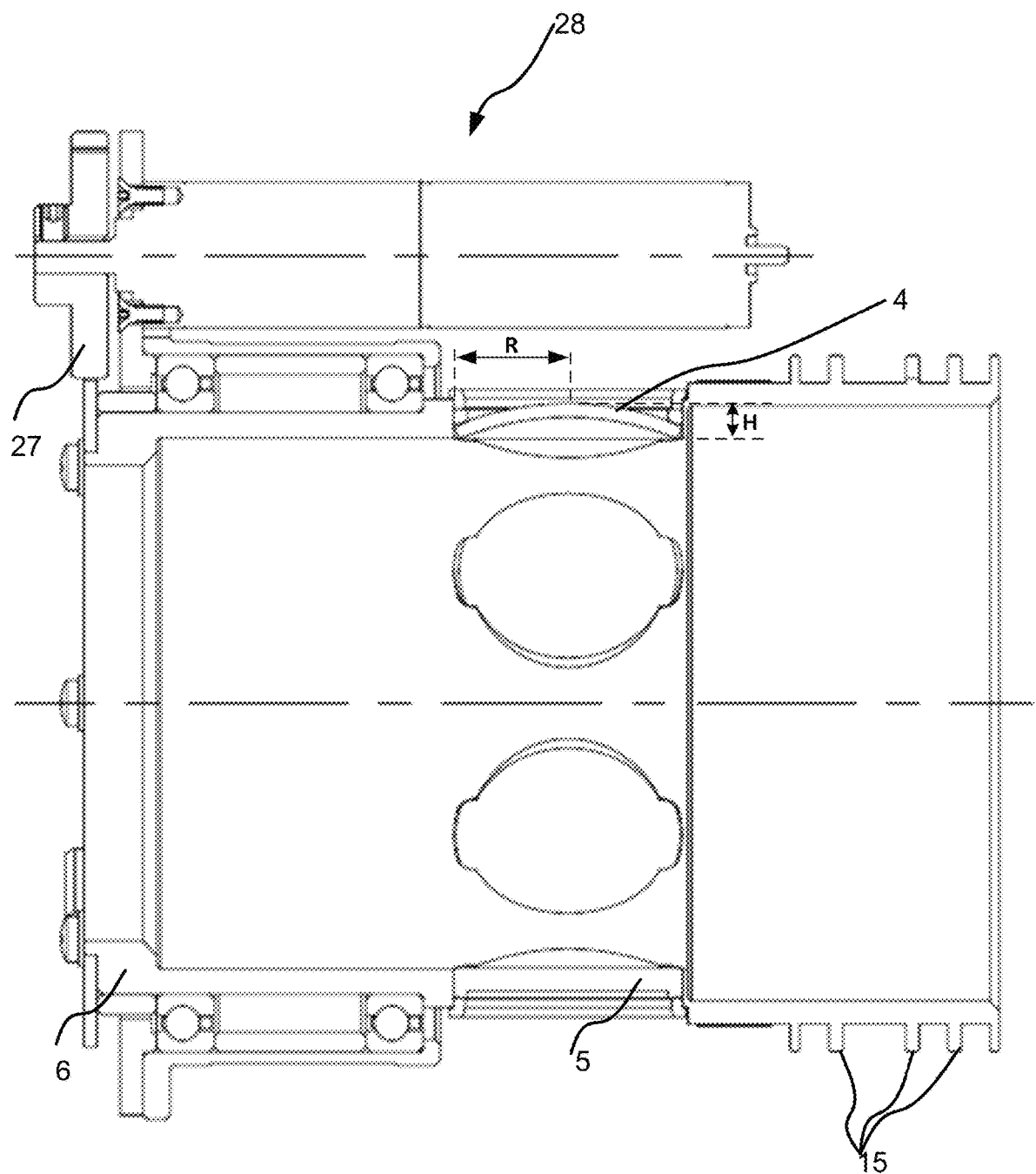
FIG. 7 shows a longitudinal section of the cylindrical element of the filter unit, shown in FIG. 6.
Figure 8:
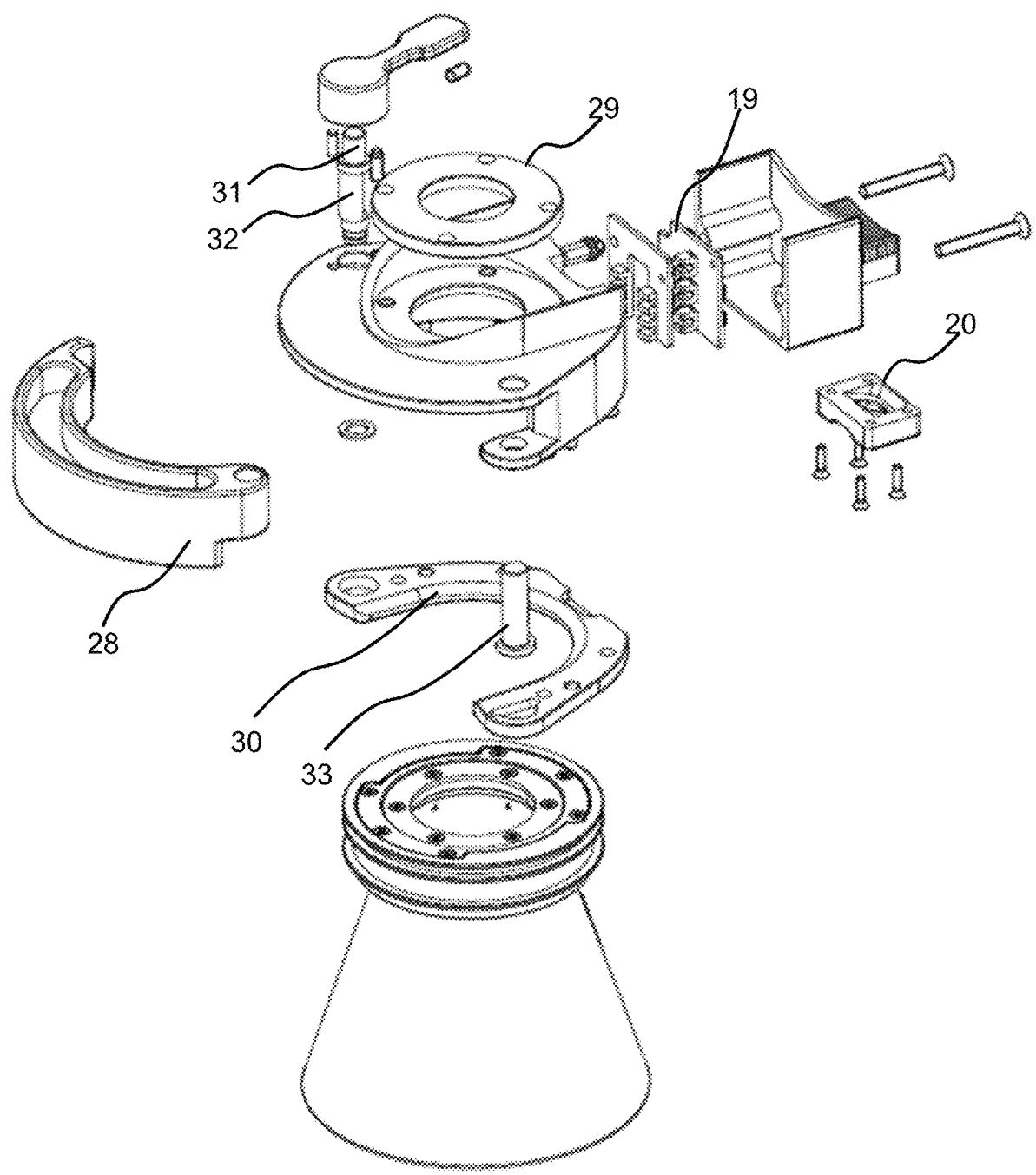
FIG. 8 shows the assembly of the collimation element unit.
Figure 9:
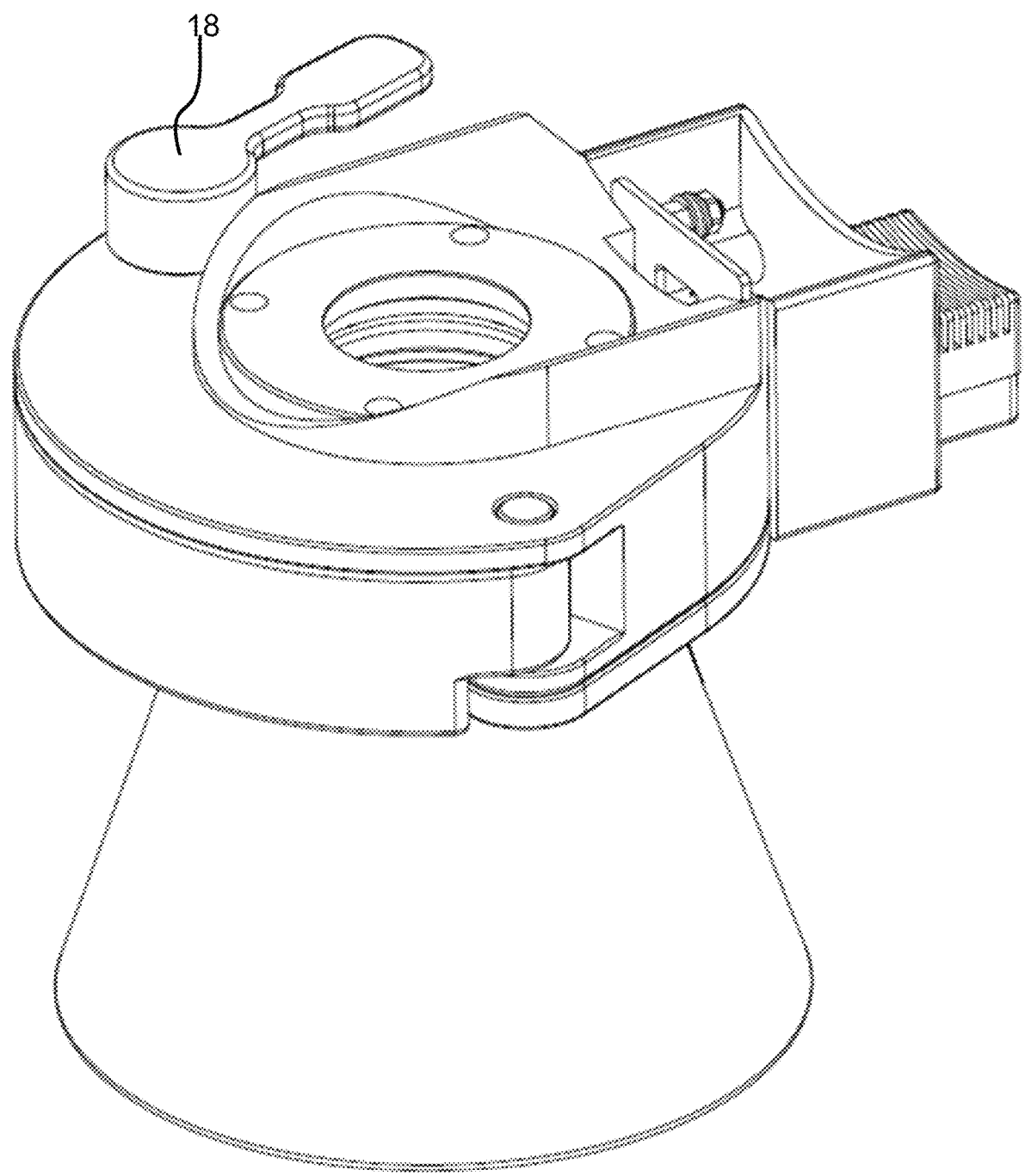
FIG. 9 shows a general view of the collimation element unit.
Figure 10:
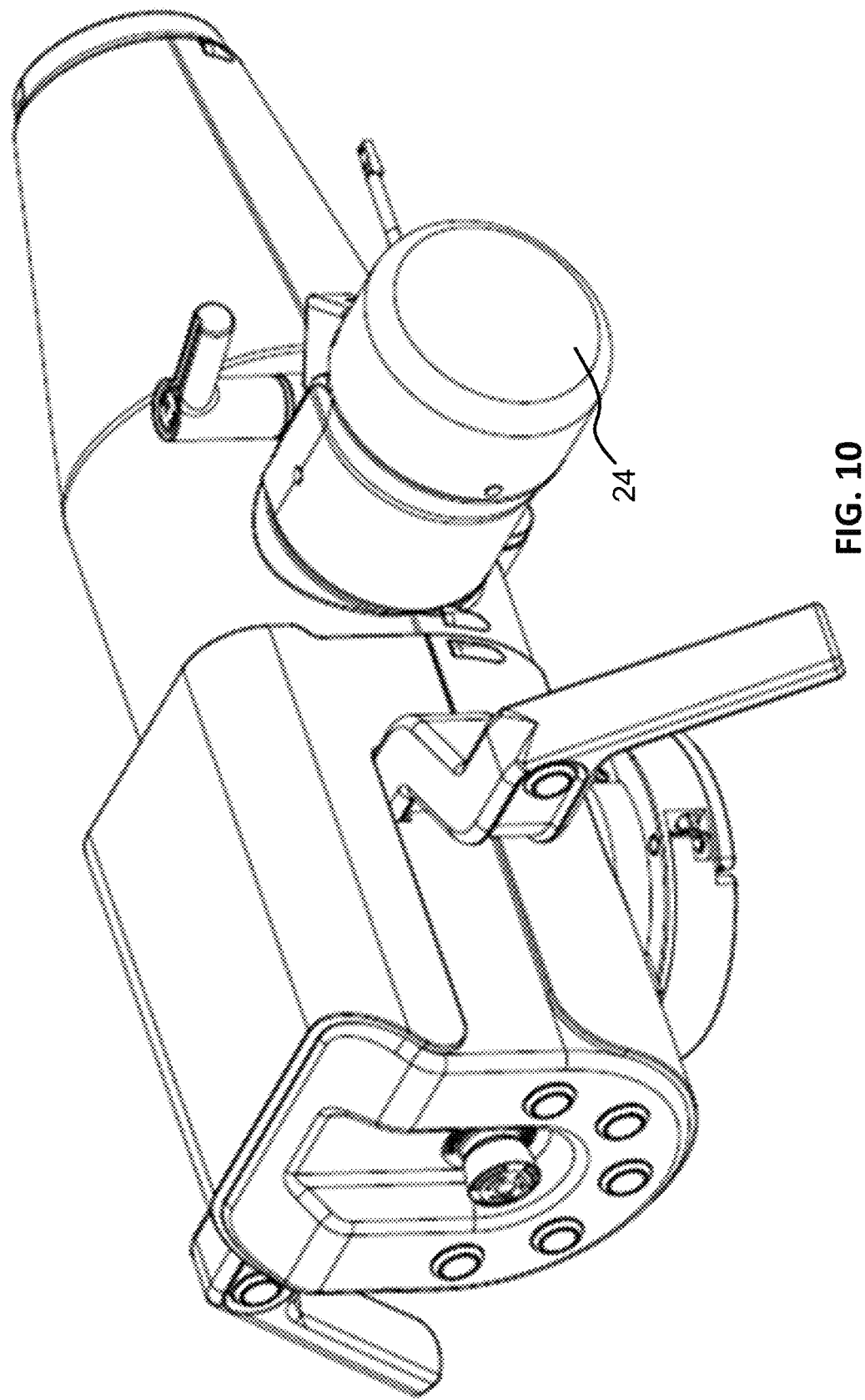
FIG. 10 shows the generator module (200 kV) with the collimation element unit and the X-ray tube rotation fixation node.
Figure 11:
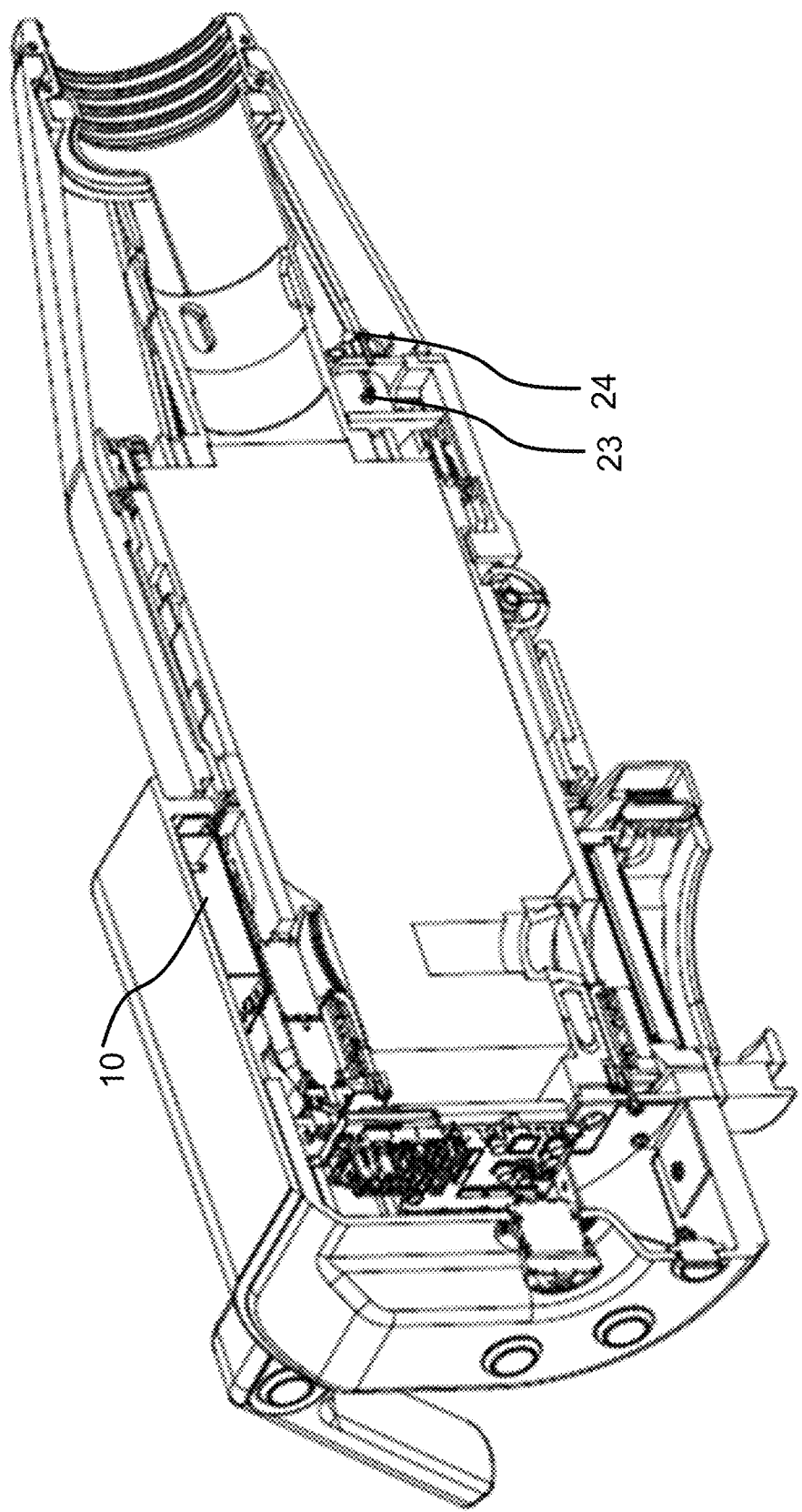
FIG. 11 shows a longitudinal section of the generator module (200 kV).

With reference to the figures, the radiation delivery system in the medical apparatus 1 comprises a generator unit 2 with an X-ray tube 26 as a source of radiation, installed in its body 21 equipped with a magnetic body rotation fixation node 22 and/or a mechanical body rotation fixation node 25; a filter unit 3 with filters (4) having segmented surface area of $S_s = 2\pi RH$ from X to Y cm$^2$ (see FIG. 1 and FIG. 7) and a plug 5 that circle a drum-shaped cylindrical element 6 equipped with slits 14 located on rings 15 that run along its outer surface 16; a filter 4 photoelectric identification system 11, with photoelectric sensors 13, 132, 133 and a controller 12; a drive unit 7 for rotating the filter unit 3; collimation elements 8, each having a set of cylindrical rings 41 and a fixation device 18 installed in a collimation unit 17 body; a collimation element 8 photoelectric identification system 19 that uses the controller 12 to control photoelectric sensors 13a, 13b, 13c of the laser system 11; an LED lighting device 20; a screen 9; and a data processing and output module 10 that produces control signals to adjust X-ray filtration characteristics.

During the assembly process of the medical apparatus 1 (see FIG. 1), the module 2 with an X-ray tube 26 as a source of radiation is installed into the body 21, which is then equipped with a magnetic body rotation fixation node 22 and/or a mechanical body rotation fixation node 25. The magnetic rotation fixation node 22 is equipped with an electromagnet 23 or an electromagnetic clutch 24, while the mechanical fixation node 25 is equipped with a clamping handle 34, a right drive axle 35 with a handle 34 rotation limiter 36, as well as a left drive axle 37, a right clamp 38 and a left clamp 39 that come into contact with the braking surface 40 of the body 21 with the X-ray tube 26.

The filter unit 3 with a plurality of filters 4 and a plug 5 that circle the cylindrical element 6 is installed, wherein the cylindrical element 6 is drum-shaped; it is equipped with two rolling bearings and connected with a gear motor 28 of the drive unit 7 capable of rotating the filter unit 3 via a gear train 27. The outer surface 16 of the cylindrical element 6 has rings 15 with slits 14 used to identify the filters 4, and the filter unit 3 is equipped with a photoelectric identification system 11, which comprises a controller 12 and photoelectric sensors 13a, 13b, 13c that are located so as to be triggered by a light beam that passes through the slits 14 in order to identify or position the filters 4. One of the rings 15 with a separate photoelectric sensor 13a is set aside for the zero position of the filter 4 in the filter unit 3; another ring 15 with a separate photoelectric sensor 13b is set aside for the working positions of the filters 4; and yet another ring 15 with a unique set of slits for each filter, equipped with photoelectric sensors 13c, is set aside for filter type identification. The filters are made in a spherical shape with the segmented surface area of $S_s=2\pi RH$ from X to Y cm$^2$ (see FIG. 1 and FIG. 7), to provide for homogeneous filtering of X-ray radiation.

Then the collimation element unit 17 is installed that is equipped with a collimation element fixation device 18 comprising a conical guide 30, a lock 28 fixed on an axis 33, an eccentric mechanism with an eccentric 32 located on the rotation handle 31 axis, a collimator 29 used to generate parallel X-ray beams, and an LED lighting device 20.

Then the collimation element photoelectric identification system 19 is mounted, which has unique collimation element identification codes, and for that purpose, each collimation element 8 has a unique set of cylindrical rings 41, which are functionally coupled with photoelectric sensors of the filter 4 identification system 11 via the controller 12. Also, the collimation element identification system 19 and the filter 4 identification system 11 are functionally coupled with the module 10 for processing and outputting data onto the screen 9 and are adapted to provide the X-ray beam with a given energy.

The radiation delivery system in the medical apparatus 1 works as follows. The operator selects an operation mode using the operator's workstation software, and then the required filter 4 is automatically selected by rotating the filter unit 3 by means of the gear train 27 that is connected to the gear motor 28 of the drive unit 7. The filter unit 3 is rotated so that its angle corresponds to the selected filter 4, while the zero position is determined with the help of the photoelectric sensor 13a. The positioning of the selected filter is checked with the help of the photoelectric sensor 13b. If necessary, the rotation angle is adjusted by rotating the filter unit 3 by means of the gear motor 28 that is controlled via the controller 12.

Then the unique code of the selected filter 4 is additionally compared with the code received from the photoelectric sensors 13c. If these two codes match, the permission to start is issued, and if they do not, the operator's workstation software 9 issues an error message, and the start is blocked. Collimation elements 8 are set up manually, then they are centered with the focal point of the X-ray tube 26 by means of the conical guide 30, and then they are fixed with the lock 28 by rotating the handle 31 with the eccentric mechanism 32.

Each collimation element has a unique code that corresponds to its unique set of cylindrical rings 41. The code is read by the collimation element 8 photoelectric identification system 19 during the collimation element 8 setup. If the received code of the collimation element 8 is among the whitelisted codes for the selected operation mode, the permission to start is issued, and if it is not, an error message is displayed on the screen 9, and the start is blocked. The working area is illuminated by an LED lighting device 20 that is turned on and off by a button located near the screen 9. In the operating position, the generator unit 1 is securely fixed by the mechanical fixation node 25 by turning the handle 34, wherein the braking surface 40 is grasped by the clamps 38, 39.

As may be seen from the above description of the radiation delivery system in the medical apparatus 1 for orthovoltage radiation therapy, the invention disclosed herein provides higher precision of filter and collimation element identification than that of the prior art, by using the filter 4 and collimation element 8 photoelectric identification system 11 that comprises photoelectric sensors 13a, 13b, 13c controlled by the controller 12, which ensures the required safety of delivering the radiation to the target area of the patient's body.

A number of identification methods can in theory be applied, such as contact identification, magnetic identification, or optical identification. Optical identification (via optoelectronic slit sensors) has been chosen because it has the following advantages:

1) Positioning accuracy (limited only by the precision with which the parts are manufactured);
2) Multiple radiation reflection resistance (since it works in the infrared range);
3) Wide product range and low price;
4) Minimum additional elements are required;
5) Works in a wide temperature range and a wide supply voltage range;
6) Can be enhanced with noise-proof coding (e.g., Gray code);
7) Resistance to contaminants (since the slit is located in the point of application only);
8) Its structure allows to place sensors in a convenient configuration depending on the filter (applicator) shape.

Having thus described a preferred embodiment, it should be apparent to those skilled in the art that certain advantages of the described method and system have been achieved.

It should also be appreciated that various modifications, adaptations, and alternative embodiments thereof may be made within the scope and spirit of the present invention. The invention is further defined by the following claims.

References (all incorporated herein by reference in their entirety):
1. X-ray therapy system XSTRAHL 150, **xstrahl.com/xstrahl-150/2.
RU Patent No. 156568 U1, issued Nov. 10, 2015.
3. U.S. Pat. No. 7,372,940 B2, issued May 13, 2008.
4. U.S. Pat. No. 7,263,170 B2, issued Aug. 28, 2007.

What is claimed, is:

1. A radiation delivery system in a medical apparatus for radiation therapy, comprising:
an X-ray generator module;
a filter unit with a plurality of filters arranged on a cylindrical element, wherein one of the filters is a lead X-ray blocker,
wherein the X-ray generator module is inside the cylindrical element;
a drive unit for rotating the filter unit;
a removable collimator having a photoelectric identification encoding for identifying the collimator; and
a processor producing control signals to the drive unit for rotating the filter unit,
wherein the filter unit includes a filter photoelectric identification system and photoelectric sensors,
wherein the cylindrical element includes slits located on rings that run along its outer surface, and
wherein the photoelectric sensors are located so as to be triggered by a light beam that passes through the slits in order to identify and/or to position the filters,
wherein a first ring with a first photoelectric sensor identifies a zero position of the filter in the filter unit, a second ring with a second photoelectric sensor identifies a working positions of the filters, and a third ring with a set of slits for each filter, and including a third photoelectric sensor, is used for filter type identification,
wherein a number of ring combinations defines a maximum number of filters.

2. The system of claim 1, wherein the filters have spherical shapes, their segmented surface area is $S_s=2\pi RH$ from X to Y $cm^2$.

3. The system of claim 1, wherein the cylindrical element is drum-shaped, and wherein the cylindrical element includes two rolling bearings and connected with a gear motor of the drive unit capable of rotating the filter unit via a gear train.

4. The system of claim 1, wherein the X-ray generator includes a magnetic body rotation fixation node that comprises a clamping handle, a right drive axle with a handle rotation limiter, a left drive axle, a right clamp and a left clamp that come into contact with a braking surface of its body with an X-ray tube of the X-ray generator, and wherein the magnetic rotation fixation node comprises electromagnets and/or an electromagnetic clutch.

5. The system of claim 1, wherein the collimator includes a lock fixed on a center axis of a filter that is currently aligned, and wherein the collimator also includes a conical guide and an eccentric mechanism with an eccentric located on a rotation handle axis.

6. The system of claim 5, wherein the photoelectric identification encoding of the collimator has unique collimation element identification codes, and each collimation element has a unique set of cylindrical rings, which are functionally coupled with the photoelectric sensors via the processor.

7. The system of claim 6, wherein the photoelectric identification encoding is functionally coupled to the processor for displaying parameters of the system onto a monitor screen and is also adapted to provide the X-ray beam with a predetermined energy.

* * * * *